(12) United States Patent
Christopher et al.

(10) Patent No.: US 9,222,110 B2
(45) Date of Patent: Dec. 29, 2015

(54) MICROORGANISM AND METHOD FOR LACTIC ACID PRODUCTION

(71) Applicant: South Dakota Board of Regents, Pierre, SD (US)

(72) Inventors: Lew P. Christopher, Rapid City, SD (US); Mohanraj Subramanian, Rapid City, SD (US); Suvarna Naga Lavanya Talluri, Rapid City, SD (US)

(73) Assignee: South Dakota Board of Regents, Pierre, SD (US)

( * ) Notice: Subject to any disclaimer, the term of this patent is extended or adjusted under 35 U.S.C. 154(b) by 0 days.

(21) Appl. No.: 14/109,587

(22) Filed: Dec. 17, 2013

(65) Prior Publication Data

US 2014/0170719 A1  Jun. 19, 2014

Related U.S. Application Data

(60) Provisional application No. 61/737,977, filed on Dec. 17, 2012.

(51) Int. Cl.
| | | |
|---|---|---|
| C12P 1/04 | (2006.01) | |
| C12P 7/56 | (2006.01) | |
| C12R 1/46 | (2006.01) | |
| C12N 9/04 | (2006.01) | |

(52) U.S. Cl.
CPC ............. *C12P 7/56* (2013.01); *C12N 9/0006* (2013.01); *C12R 1/46* (2013.01); *C12Y 101/01027* (2013.01)

(58) Field of Classification Search
CPC combination set(s) only.
See application file for complete search history.

(56) References Cited

U.S. PATENT DOCUMENTS

| | | | |
|---|---|---|---|
| 7,326,550 | B2 | 2/2008 | Porro et al. |
| 7,682,814 | B2 | 3/2010 | Park et al. |
| 2007/0021600 | A1* | 1/2007 | Doucette-Stamm et al. ... 536/23.7 |
| 2010/0190222 | A1 | 7/2010 | Ito et al. |
| 2011/0171703 | A1 | 7/2011 | Wada et al. |

OTHER PUBLICATIONS

Passos, Frederico et al., "Kinetics and Modeling of Lactic Acid Production by Lactobacillus plantarum", Applied and Environmental Microbiology, p. 2627-2636, vol. 60, No. 7, issued on Jul. 31, 1994.
Sun, Yan et al., "Modeling of continuous L(+)-lactic acid production with immobilized R. oryzae in an airlift bioreactor", Biochemical Engineering Journal 3 (1999) 87-90, 4 pages, issued on Dec. 10, 1998.
Hofvendahl, Karin et al., "Factors affecting the fermentative lactic acid production from renewable resources", Enzyme and Microbial Technology 26 (2000) 87-107, 21 pages, issued on Aug. 20, 1999.
Boonmee, Mallika et al., "Batch and continuous culture of Lactococcus lactis NZ133: experimental data and model development", Biochemical Engineering Journal 14 (2003) 127-135, 9 pages, issued on Oct. 7, 2002.
Zhou, Shengde et al., "Production of Optically Pure D-Lactic Acid in Mineral Salts Medium by Metabolically Engineered *Escherichia coli* W3110", Applied and Environmental Microbiology, Jan. 2003, p. 399-407, issued on Sep. 24, 2002.
Wee, Young-Jung et al., "Biotechnological production of L(+)-lactic acid from wood hydrolyzate by batch fermentation of *Enterococcus faecalis*", Biotechnology Letters 26: 71-74, 2004, 4 pages, issued on Nov. 5, 2003.
Zhou, S. et al., Fermentation of 12% (w/v) glucose to 1.2 M lactate by *Escherichia coli* strain SZ194 using mineral salts medium, Biotechnology Letters (2006) 28: 663-670, 8 pages, issued on Feb. 7, 2006.
Zhang, Zhan Ying et al., "Production of lactic acid from renewable materials by Rhizopus fungi", Biochemical Engineering Journal 35 (2007) 251-263, 13 pages, issued on Jan. 16, 2007.
Agarwal, Lata et al., "Anaerobic fermentative production of lactic acid using cheese whey and corn steep liquor", Biotechnol Lett (2008) 30:631-635, 5 pages, issued on Nov. 24, 2007.
Coelho, L.F. et al., "Lactic Acid Production by new *Lactobacillus plantarum* LMISM6 Grown in Molasses: Optimization of Medium Composition", Brazilian Journal of Chemical Engineering, vol. 28, No. 01, pp. 27-36, Jan.-Mar. 2011, 10 pages, issued on Sep. 27, 2010.
John, Rojan P. et al., "Fermentative production of lactic acid from biomass: an overview on process developments and future perspectives", Appl Microbiol Biotechnol (2007) 74:524-534, 12 pages, issued on Jan. 16, 2007.
Maas, Ronald H. et al., "Lactic acid production from xylose by the fungus Rhizopus oryzae", Appl Microbiol Biotechnol (2006) 72:861-868, 9 pages, issued on Mar. 10, 2006.
Narayanan, Niju et al., "L (+) lactic acid fermentation and its product polymerization", Electronic Journal of Biotechnology ISSN: 0717-3458, vol. 7, No. 2, 13 pages, issued on Aug. 15, 2004.
Wee, Young-Jung et al., "Biotechnological Production of Lactic Acid and Its Recent Applications", Food Technol. Biotechnol. 44 (2) 163-172 (2006), 10 pages, issued on Mar. 12, 2006.
Wee, Young-Jung et al., "Pilot-Scale Lactic Acid Production via Batch Culturing of *Lactobacillus* sp. RKY2 Using Corn Steep Liquor As a Nitrogen Source", Food Technol. Biotechnol. 44 (2) 293-298 (2006), 6 pages, issued on Mar. 22, 2006.

* cited by examiner

*Primary Examiner* — Kagnew H Gebreyesus
(74) *Attorney, Agent, or Firm* — McKee, Voorhees & Sease, PLC

(57) ABSTRACT

The present invention relates generally to compositions and methods for producing lactic acid using a lactic acid producing microorganism. More specifically, the present invention relates to methods for producing lactic acid with high yield, high concentration and high volumetric productivity through biological fermentation by *Enterococcus faecalis*, or recombinant microorganisms transformed to produce lactate dehydrogenase using the lactate dehydrogenase-encoding genes derived from *E. faecalis*.

5 Claims, No Drawings

SEQUENCE LISTING

<160> NUMBER OF SEQ ID NOS: 14

<210> SEQ ID NO 1
<211> LENGTH: 1282
<212> TYPE: DNA
<213> ORGANISM: Enterococcus faecalis

<400> SEQUENCE: 1
ataacaaaaa aagcacgctt cccttattta aattgttaat aaagactatt acagattggt       60
ataaccacac ctaaaaagtt cgtgatataa ttcactaaga aagaaatatt acagaaagaa      120
gagatgaacg atgaaagtat ttaacaaaaa aagtcgcaat tattggtact ggttttgttg      180
gcacaagtat tgcctattcc atgatcaacc aagggattgc gaatgaatta atcttagttg      240

-continued

| | |
|---|---|
| atattgacaa agccaaatct gaaggcgaag caattgactt attagatggt gtgtcttggg | 300 |
| gtcaagaaaa tgtaaacgtc tgggctggcg actatcaaga ctgccaagat gccgatatcg | 360 |
| tcgtgattac agctggcgct aatcaaaaac ctgggcaaag tcgtctagat ttggtttcaa | 420 |
| tcaatgcaga aattatgaaa acaattgtta acaatatcat gaaatctggt tttgatggaa | 480 |
| ttttagtgat tgcctcaaat cctgtcgatg tactgactta tgtggcttgg caagcttctg | 540 |
| gtttacctgt ttcaagagta attggaactg gtacaacttt ggacacaact cgttccgca | 600 |
| aagaactgtc tcaacgttta gcgattgatc cacgcaatgt tcacggctat attattggcg | 660 |
| aacacgggga ttctgaagtg gctgtctggt ctcataccat gattggtacc aaacctattt | 720 |
| tagaaattgt ggatacgaca gagcgcttaa ctagtgacga tttaccaatc atttctgata | 780 |
| aagtgaaaaa tacagcttat gaaattatcg atcgcaaaca agcgacctat tatgggattg | 840 |
| gtatgagtac tgcacgcatt gttaaagcca ttttaaataa tgaacaagct attttacctg | 900 |
| tctcagctta cttagatggg caatatgggc aacaagatgt atttacaggg attcctgcag | 960 |
| tcgttggcaa tcaaggtgtg actgacatta ttgaattgaa tctgaatgcc gctgaaaaag | 1020 |
| aactcttcca aaaatcagtg acacaattaa aacaagtgat ggcatcgtta caaccgaacg | 1080 |
| cttagtaatt tttaactaaa aataaacactt caactaaatt attctctacc aaaatagatt | 1140 |
| ctaattcccc tttatcgttc tttttggtac catgaaagaa gaacttcaac taaagcagaa | 1200 |
| attaggagga caaaaaatgg taatccaagg agatacgtta gaaaatagcg cacgtcgttt | 1260 |
| attgcaagaa cgtggcgtaa ca | 1282 |

<210> SEQ ID NO 2
<211> LENGTH: 1253
<212> TYPE: DNA
<213> ORGANISM: Enterococcus faecalis

<400> SEQUENCE: 2

| | |
|---|---|
| actatcactt tagcaacagg aaataaaaac tcgttgctca cgaaaaagaa tgtagaggaa | 60 |
| ggaatggtac acatgactgc agccgcaggg aataaagatc accaaaaagt aatttttagtc | 120 |
| ggggacggtg ccgtaggttc tagctatgcc tttgctttag taactcagaa tattgctcaa | 180 |
| gaagttggga ttattgatat taatgtacca aaaactgaag gagacgcgtt ggacttatct | 240 |
| cacgcattag catttacttc tcctaaaaaa atctatgctg ctacttatga cgattgccat | 300 |
| gatgcagact tagttgtctt aacagctggt gcgcctcaaa aaccaggcga aactcgttta | 360 |
| gacttagttc ataaaaactt gaaaattaat aaagaaatcg ttacaacaat tgttgattct | 420 |
| ggtttcaacg gtatcttctt agttgccgca aacccagttg atattttgac ttattcaact | 480 |
| tggaaattct ctggcttccc gaaagaacga gtaatcggtt caggaacttc actagattct | 540 |
| gctcgtttcc gtcaagcaat tgccgaatta gttgatgttg atgcacgaaa tgtccatgcc | 600 |
| tacatcttag gggaacacgg agatacgaaa ttcccagttt ggtcacatgc gaatgtcgct | 660 |
| ggcttacaaa tttacgaatg ggtgaaaaat aatcctgacg tcgatgaaga agcaatggtt | 720 |
| aatttattct tcaacgtacg cgacgctgct tacacaatca tcgagaaaaa aggagctact | 780 |
| ttctatggaa tcgcggttgc actagcgcgt atcactaaag ctatcctaaa cgatgaaaac | 840 |
| tctgtgttac cattatctgt ttatttagaa ggtgaatatg gtcaaaacga tatttatatc | 900 |
| ggtgcaccag cgatcatcaa ccgccaagga gttaaacaag tcattgaaat tccattaaca | 960 |
| gatgctgaac aagaaaaaat ggaagcttct gcttctgcat aaaagaagt tattgaaaca | 1020 |
| gcttttgcta aatttgaagc agaagaagca aaataactcc ttctataata gtcgaaaatt | 1080 |

```
aaaaacaacc aagagtgaac actattgtta ctccgcttta aagcctggta caaaaatcca    1140
aagtgatttt tgcaccaggc tttactttta atctgtttta ctttactcat cactcaactt    1200
tttcaaaaaa ttattgtttt gtttagctcg aaaataacaa tagccaaaaa taa           1253
```

<210> SEQ ID NO 3
<211> LENGTH: 294
<212> TYPE: PRT
<213> ORGANISM: Enterococcus faecalis

<400> SEQUENCE: 3

```
Met Ile Asn Gln Gly Ile Ala Asn Glu Leu Ile Leu Val Asp Ile Asp
1               5                   10                  15

Lys Ala Lys Ser Glu Gly Glu Ala Ile Asp Leu Leu Asp Gly Val Ser
            20                  25                  30

Trp Gly Gln Glu Asn Val Asn Val Trp Ala Gly Asp Tyr Gln Asp Cys
        35                  40                  45

Gln Asp Ala Asp Ile Val Val Ile Thr Ala Gly Ala Asn Gln Lys Pro
    50                  55                  60

Gly Gln Ser Arg Leu Asp Leu Val Ser Ile Asn Ala Glu Ile Met Lys
65                  70                  75                  80

Thr Ile Val Asn Asn Ile Met Lys Ser Gly Phe Asp Gly Ile Leu Val
                85                  90                  95

Ile Ala Ser Asn Pro Val Asp Val Leu Thr Tyr Val Ala Trp Gln Ala
            100                 105                 110

Ser Gly Leu Pro Val Ser Arg Val Ile Gly Thr Gly Thr Thr Leu Asp
        115                 120                 125

Thr Thr Arg Phe Arg Lys Glu Leu Ser Gln Arg Leu Ala Ile Asp Pro
    130                 135                 140

Arg Asn Val His Gly Tyr Ile Ile Gly Glu His Gly Asp Ser Glu Val
145                 150                 155                 160

Ala Val Trp Ser His Thr Met Ile Gly Thr Lys Pro Ile Leu Glu Ile
                165                 170                 175

Val Asp Thr Thr Glu Arg Leu Thr Ser Asp Asp Leu Pro Ile Ile Ser
            180                 185                 190

Asp Lys Val Lys Asn Thr Ala Tyr Glu Ile Ile Asp Arg Lys Gln Ala
        195                 200                 205

Thr Tyr Tyr Gly Ile Gly Met Ser Thr Ala Arg Ile Val Lys Ala Ile
    210                 215                 220

Leu Asn Asn Glu Gln Ala Ile Leu Pro Val Ser Ala Tyr Leu Asp Gly
225                 230                 235                 240

Gln Tyr Gly Gln Gln Asp Val Phe Thr Gly Ile Pro Ala Val Val Gly
                245                 250                 255

Asn Gln Gly Val Thr Asp Ile Ile Glu Leu Asn Leu Asn Ala Ala Glu
            260                 265                 270

Lys Glu Leu Phe Gln Lys Ser Val Thr Gln Leu Lys Gln Val Met Ala
        275                 280                 285

Ser Leu Gln Pro Asn Ala
    290
```

<210> SEQ ID NO 4
<211> LENGTH: 351
<212> TYPE: PRT
<213> ORGANISM: Enterococcus faecalis

<400> SEQUENCE: 4

```
Thr Ile Thr Leu Ala Thr Gly Asn Lys Asn Ser Leu Leu Thr Lys Lys
1               5                   10                  15

Asn Val Glu Glu Gly Met Val His Met Thr Ala Ala Gly Asn Lys
            20                  25                  30

Asp His Gln Lys Val Ile Leu Val Gly Asp Gly Ala Val Gly Ser Ser
            35                  40                  45

Tyr Ala Phe Ala Leu Val Thr Gln Asn Ile Ala Gln Glu Val Gly Ile
50                      55                  60

Ile Asp Ile Asn Val Pro Lys Thr Glu Gly Asp Ala Leu Asp Leu Ser
65                      70                  75                  80

His Ala Leu Ala Phe Thr Ser Pro Lys Lys Ile Tyr Ala Ala Thr Tyr
                85                  90                  95

Asp Asp Cys His Asp Ala Asp Leu Val Val Leu Thr Ala Gly Ala Pro
                100                 105                 110

Gln Lys Pro Gly Glu Thr Arg Leu Asp Leu Val His Lys Asn Leu Lys
            115                 120                 125

Ile Asn Lys Glu Ile Val Thr Thr Ile Val Asp Ser Gly Phe Asn Gly
            130                 135                 140

Ile Phe Leu Val Ala Ala Asn Pro Val Asp Ile Leu Thr Tyr Ser Thr
145                 150                 155                 160

Trp Lys Phe Ser Gly Phe Pro Lys Glu Arg Val Ile Gly Ser Gly Thr
                165                 170                 175

Ser Leu Asp Ser Ala Arg Phe Arg Gln Ala Ile Ala Glu Leu Val Asp
                180                 185                 190

Val Asp Ala Arg Asn Val His Ala Tyr Ile Leu Gly Glu His Gly Asp
            195                 200                 205

Thr Glu Phe Pro Val Trp Ser His Ala Asn Val Ala Gly Leu Gln Ile
            210                 215                 220

Tyr Glu Trp Val Lys Asn Asn Pro Asp Val Asp Glu Glu Ala Met Val
225                 230                 235                 240

Asn Leu Phe Phe Asn Val Arg Asp Ala Ala Tyr Thr Ile Ile Glu Lys
                245                 250                 255

Lys Gly Ala Thr Phe Tyr Gly Ile Ala Val Ala Leu Ala Arg Ile Thr
                260                 265                 270

Lys Ala Ile Leu Asn Asp Glu Asn Ser Val Leu Pro Leu Ser Val Tyr
            275                 280                 285

Leu Glu Gly Glu Tyr Gly Gln Asn Asp Ile Tyr Ile Gly Ala Pro Ala
            290                 295                 300

Ile Ile Asn Arg Gln Gly Val Lys Gln Val Ile Glu Ile Pro Leu Thr
305                 310                 315                 320

Asp Ala Glu Gln Glu Lys Met Glu Ala Ser Ala Leu Lys Glu
                325                 330                 335

Val Ile Glu Thr Ala Phe Ala Lys Phe Glu Ala Glu Ala Lys
            340                 345                 350
```

<210> SEQ ID NO 5
<211> LENGTH: 23
<212> TYPE: DNA
<213> ORGANISM: Enterococcus faecalis

<400> SEQUENCE: 5
cggagataca gaattcccag ttt    23

<210> SEQ ID NO 6

```
<211> LENGTH: 20
<212> TYPE: DNA
<213> ORGANISM: Enterococcus faecalis

<400> SEQUENCE: 6
ctttagtgat acgcgctagt                                              20

<210> SEQ ID NO 7
<211> LENGTH: 20
<212> TYPE: DNA
<213> ORGANISM: Enterococcus faecalis

<400> SEQUENCE: 7
agtggctgtc tggtctcata                                              20

<210> SEQ ID NO 8
<211> LENGTH: 21
<212> TYPE: DNA
<213> ORGANISM: Enterococcus faecalis

<400> SEQUENCE: 8
gcccatattg cccatctaag t                                            21

<210> SEQ ID NO 9
<211> LENGTH: 20
<212> TYPE: DNA
<213> ORGANISM: Enterococcus faecalis

<400> SEQUENCE: 9
tggcgatagc gagaaggata                                              20

<210> SEQ ID NO 10
<211> LENGTH: 23
<212> TYPE: DNA
<213> ORGANISM: Enterococcus faecalis

<400> SEQUENCE: 10
gtcctactct cacaaaggga aac                                          23

<210> SEQ ID NO 11
<211> LENGTH: 30
<212> TYPE: DNA
<213> ORGANISM: Enterococcus faecalis

<400> SEQUENCE: 11
gccaagcttt tgaagattaa gaaagatgta                                   30

<210> SEQ ID NO 12
<211> LENGTH: 28
<212> TYPE: DNA
<213> ORGANISM: Enterococcus faecalis

<400> SEQUENCE: 12
ggaattctta ttttgcttct tctgcttc                                     28

<210> SEQ ID NO 13
<211> LENGTH: 33
<212> TYPE: DNA
<213> ORGANISM: Enterococcus faecalis

<400> SEQUENCE: 13
gccaagctta tgaaagtatt taacaaaaaa gtc                               33
```

```
<210> SEQ ID NO 14
<211> LENGTH: 28
<212> TYPE: DNA
<213> ORGANISM: Enterococcus faecalis

<400> SEQUENCE: 14
ggaattccta agcgttcggt tgtaacga                                             28
```

MICROORGANISM AND METHOD FOR LACTIC ACID PRODUCTION

CROSS-REFERENCE TO RELATED APPLICATIONS

This application claims priority under 35 U.S.C. §119 to provisional application Ser. No. 61/737,977 filed Dec. 17, 2012, herein incorporated by reference in its entirety.

The present application contains a computer readable form of a sequence listing. The contents of the computer readable form are part of the specification and are fully incorporated herein by reference in its entirety.

FIELD OF THE INVENTION

The present invention relates generally to a method for producing lactic acid using a highly productive lactic acid producing bacterium. More specifically, the present invention relates to a method for producing lactic acid with high yield, high concentration and high volumetric productivity through biological fermentation using *Enterococcus faecalis* CBRD01.

BACKGROUND OF THE INVENTION

Lactic acid is a three carbon carboxylic acid with the molecular formula $C_3H_6O_3$ (MW=90.08), containing a hydroxyl group adjacent to the carboxyl group: α-hydroxy acid or 2-hydroxypropanoic acid. Lactic acid is soluble in water or ethanol, hygroscopic, and recognized as GRAS (Generally Regarded As Safe) by the U.S. FDA (Narayanan et al., *Electronic J. Biotechnol.* 7:167-179, 2004). In solution, lactic acid can lose a proton from the carboxyl group, producing the lactate ion ($CH_3CH(OH)COO^-$).

The applications of lactic acid in the food and other chemical industries are diverse; it is used as an acidulant/flavoring/pH buffering agent or inhibitor of bacterial spoilage in a wide variety of processed foods. For example, a technical grade lactic acid is used as an acidulant in vegetable industries. Lactic acid in food products usually serves either as a pH regulator or as a flavoring agent. A related compound that is made from lactic acid and used as a food preservative is calcium stearoyl-2-lactylate. Lactic acid is also used as a humectant or moisturizer in food processing and some cosmetics, and as a mordant, a chemical that helps fabrics accept dyes in textiles. Moreover, lactic acid is used in the pharmaceutical industry as a starting material for the synthesis of substances of pharmaceutical importance. It is also utilized in the manufacturing of lacquers and inks. In addition, lactic acid is an important component of making industrially valuable chemicals such as polylactic acid, a biodegradable plastic, ethyl lactate ($C_5H_{10}O_3$; MW=118.13) and acrylic acid ($C_3H_4O_2$; 72.06).

The global market for lactic acid has been estimated to reach 329,000 metric tons by 2015 (Global Industry Analysts Inc, January 2011). The current market price for 88% food grade lactic acid is $1,400-1,600/metric ton. Furthermore, the major lactic acid manufacturers are: PURAC; Myriant; Archer Daniels Midland Company; CSM N.V.; Galactic S.A; Henan Jindan Lactic Acid Co. Ltd.; Musashino Chemical Laboratory Ltd.; and Musashino Chemical (China) Co. Ltd. The recent announcements of plant expansions and building of new development-scale plants for producing lactic acid and/or polymer intermediates by major U.S. companies, such as Cargill, Chronopol, A.E. Staley, and Archer Daniels Midland (ADM), attest to this potential. Major international manufacturers of fermentative lactic acid include Purac (Netherlands), Galactic (Belgium), and several Chinese companies. In late 1997, Cargill joined forces with Dow Chemical and established a Cargill-Dow PLA polymer venture, NatureWorks LLC, which exists today as a stand-alone company. NatureWorks LLC has constructed a major lactic acid facility in Blair, Nebr., which has the capacity of producing 180,000 metric tons of lactic acid per year, and it began operating in late 2002. The growing lactic acid market is and will in future be driven largely by rising oil prices, stringent government regulations and greater consumer interest toward the use of greener products (Global Industry Analysts Inc, January 2011).

Lactic acid can be produced via chemical synthesis or biological fermentation. In chemical synthesis (Narayanan et al., *Electronic J. Biotechnol.* 7:167-179, 2004), hydrogen cyanide (HCN) is first added to acetaldehyde ($CH_3CHO$) in presence of a catalyst to produce lactonitrile ($CH_3CHOHCN$). This reaction occurs in liquid phase at high atmospheric pressures. The crude lactonitrile is recovered and purified by distillation. Lactonitrile is then hydrolyzed to lactic acid, either by concentrated hydrochloric acid (HCl) or by sulfuric acid ($H_2SO_4$) to produce the corresponding ammonium salt and lactic acid ($CH_3CHOHCOOH$). Lactic acid is then esterified with methanol ($CH_3OH$) to produce methyl lactate ($CH_3CHOHCOOCH_3$) which is removed and purified by distillation and hydrolyzed by water under acid conditions to produce lactic acid and methanol, according to the Eqs. 1-4:

$$CH_3CHO + HCN \rightarrow CH_3CHOHCN \qquad \text{Eq. 1}$$

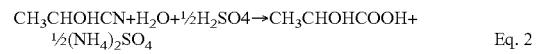
$$CH_3CHOHCN + H_2O + \tfrac{1}{2}H_2SO_4 \rightarrow CH_3CHOHCOOH + \tfrac{1}{2}(NH_4)_2SO_4 \qquad \text{Eq. 2}$$

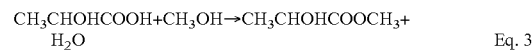
$$CH_3CHOHCOOH + CH_3OH \rightarrow CH_3CHOHCOOCH_3 + H_2O \qquad \text{Eq. 3}$$

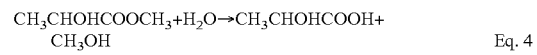
$$CH_3CHOHCOOCH_3 + H_2O \rightarrow CH_3CHOHCOOH + CH_3OH \qquad \text{Eq. 4}$$

The chemical synthesis route produces a racemic mixture of D(−)-lactic acid and L(+)-lactic acid, which are not suitable for some specific applications like synthesis of polylactic acid (PLA), one of the most promising end-use markets for lactic acid. Hence, about 90% of current commercial lactic acid is obtained via biological fermentation of sugars (Hofvendahl and Hahn-Hägerdal, *Enzyme Microbiol. Technol.* 26: 87-107, 2000; Zhou et al. *Biotechnol. Lett.* 28:663-670, 2006). Biological fermentation of sugars produces stereospecific D(−)-lactic acid or L(+)-lactic acid depending on the strains used. For example, the microorganisms *Lactobacillus, Bacillus, Rhizopus, Streptococcus*, and *Enterococcus* produce L(+)-lactic acid while microorganisms such as *Leuconostoc* and *Lactobacillus vulgaricus* produce D(−)-lactic acid (U.S. Pat. No. 7,682,814).

L(+)-lactic acid is the preferred component for many food and industrial applications. L(+)-lactic acid is currently produced via biological fermentation utilizing lactic acid bacteria (LAB) or fungi such as *Rhizopus* (Maas et al., *Appl. Microbiol. Biotechnol.* 72:861-868, 2006). Some recombinant yeast strains have also been demonstrated to enhance lactic acid production from various carbon feedstocks (U.S. Pat. No. 7,326,550). However, as both yeast and fungal strains have low yield and productivity of lactic acid, compared to LAB, they are generally not preferred for industrial production of lactic acid. In addition, the mycelial morphology of fungal strains can result in increased viscosity of the fermentation medium and can cause blockages around the impellers (Sun et al., *Biochem. Eng. J.* 3:87-90, 1999).

Most industries use recombinant *Lactobacillus* sp. for lactic acid production. However, it is known that most *Lactobacillus* strains are fastidious that require expensive nutritional components and complex organic substances to support their growth and metabolisms as the LAB cannot generate most of the growth regulatory factors on their own. The desirable characteristics of industrial microorganisms are their ability to rapidly ferment inexpensive feedstocks, requiring minimal amount of nitrogenous substances, and produce high yields of stereo-specific lactic acid with low amounts of byproducts. Furthermore, as the purity of food-grade lactic acid supplied by the industries is on average between 80% and 90%, production of a pharmaceutical-grade lactic acid with purity higher than 90% will increase the cost of purification of lactic acid, which in turn will reflect on its price (John et al., *Appl. Microbiol. Biotechnol.* 74:544-534, 2007). Accordingly, there is a need for a method of lactic acid production with high titer, yield and volumetric productivity utilizing a less fastidious microorganism capable of growing on simple and inexpensive fermentation medium.

Recent studies and research developments, as presented in the referenced patents and incorporated in their entirety below, describe the use of wild-type and recombinant microorganisms for lactic acid production. However, to date, no patent literature has described the use of *Enterococcus faecalis* for lactic acid production. In published research literature, *E. faecalis* RKY1 was used to produce up to 93 g/L lactic acid at 1.7-3.2 g/L/h and pH 7.0 on wood hydrolyzate containing up to 100 g/l glucose equivalents and supplemented with 15 g/l yeast extract (Wee et al., *Biotechnol. Lett.* 26:71-74, 2004). Another *Enterococcus* species, *E. flavescens*, produced 28 g lactic acid/L at pH 5.5 on cheese whey as carbon source and corn steep liquor as nitrogen source under controlled anaerobic conditions after 30 h of fermentation (Agarwal et al., *Biotechnol. Lett.* 30:631-635, 2008).

U.S. Pat. No. 4,698,303, granted on Oct. 6, 1987, discloses a method of producing lactic acid by *Lactobacillus casei* at a cell mass concentration of 60 g/L, using continuous fermentation employing medium pretreatment, cell-recycle fermentation, fermentation broth acidification, and lactic acid separation. Enzymatic digest of whey was used as a nitrogen base in the culture medium. The fermentation was carried out at pH 5.0-6.5 and temperature 40° C.-45° C. utilizing lactose as a carbon source at a feed rate of 0.25 fermentor volumes/h. The yield and rate of lactate production was above 90% and 12 g/L/h, respectively. However, the specific productivity was very low (0.2 g lactate/g dry cell/h).

U.S. Pat. No. 7,326,550, granted on Feb. 5, 2008, describes the production of lactic acid utilizing recombinant yeast strains. According to the patent, yeast strains such as *Kluyveromyces lactis*, *Torulaspora delbrueckii*, *Saccharomyces* sp. and *Zygosacchoromyces bailii*, lacking ethanol production ability or with reduced ethanol production ability and/or reduced pyruvate dehydrogenase and pyruvate decarboxylase activities, were transformed with a copy of the gene encoding lactic dehydrogenase (LDH), functionally linked with a promoter sequence of the yeasts or with a heterologous expression by overexpressing a lactate promoter. The recombinant yeasts produced 0.052-0.757 g lactic acid/g glucose in a medium containing 1% yeast extract, 2% peptone and 10% glucose. A maximum concentration of 109 g/L of free lactic acid was achieved with a *Kluveromyces* yeast carrying LDH gene, designated PMI/C1[pEPL2], however, the final yield and productivity of lactic acid decreased to 0.59 g/g glucose and 0.795 g/L/h, respectively. The fermentation medium was enriched with expensive complex substrates like yeast extract and peptone that represent significant obstacles to industrial scale up.

In U.S. Pat. Pub. No. 2010/0190222, published on Jul. 29, 2010, a method of producing and separating lactic acid in a culture medium from fermentation culture is described. Lactic acid was produced by recombinant yeast strains using glucose at 10% as a carbon source for 72 h. The final lactic acid yield of 26% and productivity of 0.36 g/L/h are very low for commercial utilization.

In U.S. Pat. No. 7,682,814, granted on Mar. 23, 2010, a method of producing lactic acid at high concentration and high yield was described using the strain *Lactobacillus paracasei* CJLA0310 KCCM-10542. This strain was shown to produce 179 g/L of lactic acid from 180 g/L of glucose (yield of 99.5%) with an average productivity of 3.85 g/L/h a high cell density culture ($OD_{600}$ of 24). Although the lactic acid yield and titer are high, this organism was cultivated in a nutrient-rich fermentation medium containing large amounts of complex organic substances such as yeast extract (15 g/L) and peptone (10 g/L) which is believed to increase the cost of lactic acid production and purification from the complex medium (Narayanan et al., *Electronic J. Biotechnol.* 7:167-179, 2004).

U.S. Pat. No. 2011/0171703, published on Jul. 14, 2011, discloses a recombinant bacterium, *Escherichia coli*, transformed with a gene encoding one NAD-dependent lactate dehydrogenase and one NAD-independent lactate oxidoreductase. The recombinant *E. coli* produced 97 g lactic acid/L in a culture medium containing 120 g glucose/L and 30 g yeast extract/L at pH 7.5 in 18 h. Drawbacks of this method are the relatively low lactic acid yield (80%) and the use of high amounts of yeast extract as a nitrogen base which leads to increased production and purification costs.

SUMMARY OF THE INVENTION

The embodiments disclosed below satisfy this need. The following simplified summary is provided in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

The present invention provides a method and microorganism for producing high titers and yields of lactic acid with a high volumetric productivity. In one embodiment the lactic acid is produced from a lactate dehydrogenase producing microorganism containing SEQ ID NO: 1 or SEQ ID NO: 2. This lactate dehydrogenase producing microorganism may be, for example, isolated and identified as *Enterococcus faecalis* (referred to herein as strain CBRD01 and deposited as ATCC Accession Number PTA-12846). As used herein, this designation includes derivative strains. In alternate embodiments the microorganism may be a yeast or a different bacterium.

The microorganism produces lactate dehydrogenase which converts pyruvate and reduced nicotinamide adenine dinucleotide (NADH) into lactic acid and oxidized nicotinamide adenine dinucleotide (NAD+).

In another embodiment, the invention is a nucleic acid sequence according to SEQ ID NO: 1 or SEQ ID NO: 2 that encodes lactate dehydrogenase, wherein the lactate dehydrogenase is according to SEQ ID NO: 3 or SEQ ID NO: 4, respectively. The gene sequence may be functionally associated with one or more regulatory gene sequences. In yet another embodiment, the invention is a cloning or expression vector that includes nucleic acid sequences according to SEQ ID NO: 1 or SEQ ID NO: 2, or both SEQ ID NO: 1 and SEQ ID NO: 2.

According to the present invention, the method of producing lactic acid may be by cultivating the microorganism in a fermentation medium containing a carbon source. The microorganism may be *E. faecalis* (ATCC Accession Number PTA-12846). In one embodiment, the fermentation medium may include a mineral salt.

The method may include less than 25 mM glucose in the fermentation medium. It may also include less than 3 g yeast extract per liter. In one respect the method may result from a yield greater than 90% of the theoretical maximum on glucose at the end of fermentation. Furthermore, the lactic acid may be produced in a volumetric amount greater than 7 g/L/h at the end of fermentation.

The cell density of the microorganism may reach greater than 3 g biomass per liter of culture medium with an optical density $OD_{600}$ of the medium being less than 12.

The carbon source may be a simple sugar, a sugar oligomer, a sugar polymer, a sugar alcohol, or mixtures thereof.

Other aspects of the invention are found throughout the specification.

DETAILED DESCRIPTION OF THE PREFERRED EMBODIMENTS

The present invention relates generally to a method for producing lactic acid using a lactic acid producing bacterium. More specifically, the present invention relates to a method for producing lactic acid with high yield, high concentration and high volumetric productivity through biological fermentation using *E. faecalis* strain CBRD01 or a recombinant microorganism strain containing the lactate dehydrogenase-encoding gene sequences from this organism.

In the description that follows, a number of terms used in the fields of biology and chemistry are extensively utilized. The following non-limiting definitions provide a clear and consistent understanding of the specification and claims, including the scope to be given such terms.

When the terms "one," "a," or "an" are used in this disclosure, they mean "at least one" or "one or more," unless otherwise indicated.

The terms "invention" or "present invention" as used herein are intended to be non-limiting and are not intended to refer to any single embodiment of the particular invention but encompasses all possible embodiments as described in the specification and the claims.

The term "fermentation" as used herein refers to a process in which one or more substrates present in a fermentation medium are converted by a microorganism (or isolate and/or variant thereof) to a product, such as lactate. While fermentation may occur under anaerobic conditions, it is not intended that the term be solely limited to strict anaerobic conditions, as fermentation also occurs in the presence of oxygen.

The term "fermentation medium" as used herein refers to the environment in which fermentation is carried out and which includes the fermentation substrate, such as the carbohydrate source that is metabolized by the microorganism (or isolate and/or variant thereof). Furthermore, the "fermentation medium" may comprise nutrients and/or growth stimulators for the fermenting microorganism(s). Nutrient and growth stimulators are widely used in the art of fermentation and include nitrogen sources, such as ammonia, urea, vitamins and minerals, or combinations thereof.

The terms "isolated bacteria" and "isolated bacterial strain" are meant to refer to a composition in which the bacteria are substantially or essentially free from components such as other microorganisms that normally accompany it in its native state., e.g., in a culture, such as when separated from its naturally occurring environment. As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi.

The term "lactic acid" refers to 2-hydroxypropionic acid in either free acid or salt form. The salt form of lactic acid is referred to as "lactate" regardless of the neutralizing agent, i.e., calcium carbonate or ammonium hydroxide. As referred to herein, lactic acid can refer to either stereoisomeric form of lactic acid (L(+)-lactic acid or D(−)-lactic acid). Further, the term lactate can refer to either stereoisomeric form of lactate (L(+)-lactate or D(−)-lactate).

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

As used herein, the term "mutant" comprises one or more, preferably one or several, deletions, substitutions or additions in the amino acid or nucleotide sequences of the proteins of the present invention, or homologues thereof. The mutant may include either naturally occurring mutants or artificial mutants.

Where the mutant is a protein or polypeptide, preferable substitutions are conservative substitutions, which are substitutions between amino acids similar in properties such as structural, electric, polar, or hydrophobic properties. For example, the substitution can be conducted between basic amino acids (e.g., Lys, Arg, and His), or between acidic amino acids (e.g., Asp and Glu), or between amino acids having non-charged polar side chains (e.g., Gly, Asn, Gln, Ser, Thr, Tyr, and Cys), or between amino acids having hydrophobic side chains (e.g., Ala, Val, Leu, Ile, Pro, Phe, and Met), or between amino acids having branched side chains (e.g., Thr, Val, Leu, and Ile), or between amino acids having aromatic side chains (e.g., Tyr, Tip, Phe, and His).

The term "conservatively modified variants" applies to both amino acid and nucleic acid sequences. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
See also, Creighton (1984) Proteins W.H. Freeman and Company.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)).

As used herein "full-length sequence" in reference to a specified polynucleotide or its encoded protein means having the entire amino acid sequence of a biologically active form of the specified protein. Methods to determine whether a sequence is full-length are well known in the art including such exemplary techniques as northern or western blots, primer extensions, S1 protection, and ribonuclease protection. See, e.g., Plant Molecular Biology: A Laboratory Manual, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a sub-sequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein, "lactate dehydrogenase" refers to a protein gene product that has lactic acid producing activity, and in particular converts pyruvate and reduced nicotinamide adenine dinucleotide (NADH) into lactic acid and oxidized nicotinamide adenine dinucleotide (NAD+). In one aspect of the invention, lactates dehydrogenase include proteins with at least 75% identity to SEQ ID NO:3 or 4 that has lactic acid producing activity.

As used herein "promoter" includes reference to a region of DNA upstream from the start of transcription and involved in recognition and binding of RNA polymerase and other proteins to initiate transcription. Examples of promoters under developmental control include promoters that preferentially initiate transcription at different points in the development of a microorganism, etc. A "cell type" specific promoter primarily drives expression in certain cell types in a life cycle. An "inducible" or "repressible" promoter is a promoter which is under environmental control. Examples of environmental conditions that may affect transcription by inducible promoters include anaerobic conditions, the presence of a specific molecule, or the presence of light. Cell type specific and inducible promoters constitute the class of "non-constitutive" promoters. Examples of inducible promoters include Cu-sensitive promoter, Gal1 promoter, Lac promoter, while Trp promoter, Nit1 promoter and cytochrome c6 gene (Cyc6) promoter are among repressible promoters. A "constitutive" promoter is a promoter which is active under most environmental conditions. Examples of constitutive promoters include Ubiquitin promoter, actin promoter, PsaD promoter, RbcS2 promoter, heat shock protein (hsp) promoter variants, and the like.

A skilled person appreciates a promoter sequence can be modified to provide for a range of expression levels of an operably linked heterologous nucleic acid molecule. Less than the entire promoter region can be utilized and the ability to drive expression retained. However, it is recognized that expression levels of mRNA can be decreased with deletions of portions of the promoter sequence. Thus, the promoter can be modified to be a weak or strong promoter. A promoter is classified as strong or weak according to its affinity for RNA polymerase (and/or sigma factor); this is related to how closely the promoter sequence resembles the ideal consensus sequence for the polymerase. Generally, by "weak promoter" is intended a promoter that drives expression of a coding sequence at a low level. By "low level" is intended levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts. The term "operably connected" or "operably linked" in the present context means placing a structural gene under the regulatory control of a promoter which then controls expression of the gene. Promoters and the like are generally positioned 5' (upstream) to the genes which they control. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting, i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting, i.e. the genes from which it is derived.

As used herein "recombinant" or "engineered" includes reference to a cell or vector that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "expression", as used herein, refers to the transcription and stable accumulation of coding (mRNA) or functional RNA derived from a gene. Expression may also refer to translation of mRNA into a polypeptide. "Overexpression" refers to the production of a gene product in transgenic organisms that exceeds levels of production in normal or non-transformed organisms.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

As used herein, "vector" includes reference to a nucleic acid used in transfection of a host cell and into which can be inserted a polynucleotide. Vectors are often replicons. Expression vectors permit transcription of a nucleic acid inserted therein. The vectors may contain a selectable marker or reporter gene necessary for screening transformed cells of interest. Examples of the selectable marker include, but are not limited to, drug resistant genes such as kanamycin resistant gene (NPTII), hygromycin resistant gene (htp), biarafos resistant gene, carbenicillin resistant gene, and the like. Examples of the reporter gene include, but are not limited to, GFP (green fluorescence protein) gene, GUS (beta.-glucuronidase) gene, luciferase gene, and beta.-galactosidase gene. The vector may also include other regulatory sequences such as promoters, enhancers, initiators, terminators, splice sites. Expression vectors permit transcription of a nucleic acid inserted therein. The vectors may contain a selectable marker or reporter gene necessary for screening transformed cells of interest. Examples of the selectable marker include, but are not limited to, drug resistant genes such as kanamycin resistant gene (NPTII), hygromycin resistant gene (htp), biarafos resistant gene, carbenicillin resistant gene, and the like. Examples of the reporter gene include, but are not limited to, GFP (green fluorescence protein) gene, GUS (.beta.-glucuronidase) gene, luciferase gene, and .beta.-galactosidase gene. Vectors are known or can be constructed by those skilled in the art and should contain all expression elements necessary to achieve the desired transcription of the sequences. Other beneficial characteristics can also be contained within the vectors such as mechanisms for recovery of the oligonucleotides in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either prokaryotic or eukaryotic host systems. One of ordinary skill in the art will know which host systems are compatible with a particular vector. The vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al., BioTechniques 4:504-512 (1986) and include, for example, stable or transient transfection, lipofection, electroporation and infection with recombinant viral vectors.

Bacterial Strain

The present invention discloses the discovery of a bacterial strain that is capable of producing the industrially valuable chemical, lactic acid, with high yield and high concentration through biological fermentation. More specifically, it was discovered that L(+)-lactic acid can be produced efficiently from this bacterium that was isolated from solid waste and identified as E. faecalis CBRD01. As lactic acid produced through biological fermentation is utilized for many industrial applications, the present invention provides a method for producing lactic acid that significantly decreases the current costs of producing lactic acid both for industrial production and its related purification.

A "derivative strain" refers to any bacterial strain or isolate that is generated from Enterococcus faecalis CRBD01 by transformation, selective culturing, genome shuffling, or the like, and includes all lactic acid producing bacteria with the characteristics set out in Table 1.

An exemplary bacterial strain was isolated from samples collected from solid waste facilities in Rapid City, S. Dak. The strain was identified as Enterococcus faecalis CRBD01 and it was deposited on Apr. 19, 2012 with the American Type Culture Collection (ATCC®), Manassas, Va., USA and given the following accession number: PTA-12846. Access to these deposits will be available during the pendency of the application to the Commissioner of Patents and Trademarks and persons determined by the Commissioner to be entitled thereto upon request. This deposit was made merely as a convenience for those of skill in the art and is not an admission that a deposit is required under 35 U.S.C. §112.

Lactic Acid Production

According to one aspect of the invention, lactic acid can be produced by E. faecalis CBRD01 in a fermentation medium containing a carbon source, such as a sugar, and in particular glucose. In one embodiment of the present invention, E. faecalis CBRD01 may be cultivated in a fermentation medium containing glucose as the carbon source. In a more preferred embodiment, E. faecalis CBRD01 produces lactic acid at a concentration of 182.1 g/L lactic acid after 38 h of incubation, for example using a fed-batch process. In an even more preferred embodiment, the bacterium E. faecalis CBRD01 utilizes only 2-8% of the available carbon in the fermentation medium for its growth and energy metabolism, while the rest (92-98%) was converted to lactic acid. As such, in this exemplary embodiment, the present invention provides a microorganism that requires less nutrients and is capable of producing a greater than 92% yield of lactate with a high titer of at least 88 g/L under fed batch cultivation with a low cell density of 12 $OD_{600}$.

Endogenous lactate dehydrogenase activity in lactic acid producing bacteria converts pyruvate to lactate. Lactic acid producing bacteria may have one or more genes, typically one, two or three genes, encoding lactate dehydrogenase.

In one aspect of the invention, a microorganism comprises at least one gene sequence that encode a lactate dehydrogenase, wherein said lactate dehydrogenase effects lactic acid production. In a preferred embodiment, the gene sequence the encodes lactate dehydrogenase comprises a nucleotide sequence that is at least 75% homologous to gene 1 (RNHR02052) and/or gene 2 (RNHR01261). In a preferred embodiment of the invention, the microorganism is the bacterium E. faecalis CBRD01. Lactate dehydrogenase gene 1 (RNHR02052) comprises the nucleotide sequence of SEQ ID NO: 1, and the amino acid sequence of SEQ ID NO: 3. Lactate dehydrogenase gene 2 (RNHR01261) comprises the nucleotide sequence of SEQ ID NO: 2, and the amino acid sequence of SEQ ID NO: 4, as shown below.

The gene sequence or sequences according to the present invention may be an endogenous gene sequence or a heterologous gene. In one aspect, the sequence encodes a lactate dehydrogenase, wherein the sequence comprises a nucleotide sequence selected from the group consisting of: (a) a nucleotide sequence comprising the sequence set forth in SEQ ID NO: 1 or 2; (b) a nucleotide sequence comprising at least 50 contiguous nucleotides of the sequence of SEQ ID NO: 1 or 2, wherein said nucleotide sequence encodes a lactate dehydrogenase; (c) a nucleotide sequence having at least 75% sequence identity across the entire polynucleotide to the sequence of SEQ ID NO: 1 or 2 wherein said nucleotide sequence encodes a lactate dehydrogenase; or (d) a nucleotide encoding a protein having at least 75% sequence identity to SEQ ID NO:3 or 4. In a more preferred embodiment, the sequence comprises both SEQ ID NO:1 and 2 or homologues thereof.

In particular, the primary reaction catalyzed by RNHR01261 and RNHR02052 proteins is the conversion of pyruvate to lactate, as shown in the equation 5 below:

Pyruvate+NADH ↔ Lactate+NAD⁺  Eq. 5

Furthermore, other reactions believed to be catalyzed by RNHR01261 and RNHR02052 are as follows (Eqs. 6-9):

3-Mercaptolactate+NAD⁺ ↔ Mercaptopyruvate+
NADH+H⁺  Eq. 6

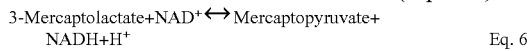

Glyoxylate+NADH ↔ Oxalate+NAD⁺  Eq. 7

2-Hydroxybutanoic acid+NAD⁺ ↔ 2-Oxobutanoate+
NADH+H⁺  Eq. 8

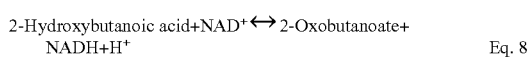

(S)-Lactate+NAD⁺ ↔ Pyruvate+NADH+H⁺  Eq. 9

In one exemplary embodiment of the present invention, lactic acid can be produced in a reaction mixture by contacting a culture of *E. faecalis* CBRD01 with a carbohydrate source such as glucose. The *E. faecalis* CBRD01 bacterial strain of the present invention can be cultured in any suitable medium according to known methods. More specifically, the culture conditions employed, including temperature, pH, aeration or anaerobic sparging rate, agitation rate, culture duration, and the like, may be determined empirically by one of skill in the art to maximize production of lactic acid from the bacteria of the present invention. In a preferred embodiment, the lactic acid production according to the methods of the present invention result in at least 80% of the carbon source in the medium being converted into lactic acid. In a more preferred embodiment, at least 90% of the carbon source in the medium is converted into lactic acid.

In another aspect, the lactic acid production according to the methods of the present invention is conducted at an acidic pH. In a preferred embodiment, the pH is between about 6.0 and 3.0.

Fermentation Media

A suitable fermentation medium refers to any medium in which a microorganism of the present invention, when cultured, is capable of producing lactate. In some embodiments, such a medium is an aqueous medium comprising assimilatable carbon, nitrogen, and phosphate sources. Such a medium can also include appropriate salts, minerals, metals, or other nutrients. However, as discussed, it should be recognized that a variety of fermentation conditions are suitable and can be selected by those skilled in the art.

In various embodiments, sources of assimilatable carbon which can be used in a suitable fermentation medium include, but are not limited to, sugars and their polymers, including, dextrin, sucrose, maltose, lactose, glucose, fructose, galactose, mannose, sorbose and sugar alcohol such as glycerine. Exemplary embodiments of the present invention utilize monosaccharides, disaccharides and trisaccharides. In one embodiment, the preferred carbon source is glucose.

Microorganisms of the present invention can be cultured in conventional fermentation modes, which include, but are not limited to, normal batch fermentations, fed-batch fermentations, continuous fermentations or any suitable fermentation process known to one of skill in the art. In certain embodiments, it may be desirable to perform fermentations under reduced oxygen or anaerobic conditions. Moreover, lactic acid may be recovered according to any known methods including distillation, ion exchange chromatography, gel filtration, solvent extraction, affinity chromatography or any combination thereof.

Cloning

In one aspect, the invention includes a cloning or expression vector containing one or both genes according to SEQ ID NO: 1 and SEQ ID NO: 2. In a preferred embodiment, the nucleotide sequence or sequences encoding a lactate dehydrogenase is/are operably linked to a promoter sequence. In a more preferred embodiment, the vector comprises both SEQ ID NO:1 and SEQ ID NO:2. In another preferred embodiment, SEQ ID NO:1 is operably linked to a first promoter sequence, and SEQ ID NO:2 is operably linked to a second promoter sequence. Additionally, it would be within reasonable experimentation to produce such a cloning vector using molecular biology techniques.

In another aspect of the present invention, a microorganism that expresses a lactate dehydrogenase and produces lactic acid is provided. Methods of transforming microorganisms are well understood in the art. The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms. It would be within the skill in the art to determine transformation of a microorganism with a vector encoding a lactate dehydrogenase simply by assaying for conversion of pyruvate and NADH to lactate and NAD+ by a microbe transformed with such a cloning or expression vector.

Oligonucleotide sequences can be introduced into cells, including microorganisms, as is known in the art. Transfection, electroporation, fusion, liposomes, colloidal polymeric particles and viral and non-viral vectors as well as other means known in the art may be used to deliver the oligonucleotide sequences to the cell. The method of delivery selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like.

Physical methods of introducing oligonucleotides or nucleic acid molecules include injection of a solution containing the nucleic acid, bombardment by particles covered by the nucleic acid, soaking the cell or organism in a solution of the nucleic acid, or electroporation of cell membranes in the presence of the nucleic acid. A viral construct packaged into a viral particle would accomplish both efficient introduction of an expression construct into the cell and transcription of nucleic acid molecules encoded by the expression construct. Other methods known in the art for introducing nucleic acids to cells may be used, such as lipid-mediated carrier transport, chemical-mediated transport, such as calcium phosphate, and the like.

As described supra and in the art, oligonucleotide reagents may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated in its entirety herein by reference).

The present invention also provides vectors comprising an expression control sequence operatively linked to the oligonucleotide sequences of the invention. The present invention further provides host cells, selected from suitable eukaryotic and prokaryotic cells, which are transformed with these vectors as necessary. Such transformed cells allow the study of the function and the regulation of malignancy and the treatment therapy of the present invention.

Hereinafter, the invention is described in detail with reference to the following examples. It is to be understood, however, that these examples are for illustrative purposes only and are not construed to limit the scope of the present invention.

EXAMPLES

Example 1

This example illustrates the sample collection and enrichment medium for obtaining lactic acid producing bacteria.

Sludge and soil samples were collected from a material recovery and composting facility in Rapid City, S. Dak., USA. The samples were placed in sterile serum bottles containing culture enrichment medium and tightly sealed with stoppers. The samples were processed for selective culture enrichment with different substrates. The culture enrichment medium for lactic acid production had the following components: salts, iron, trace elements, yeast extract, and glucose. The medium was supplemented with 100 mM potassium phosphate buffer at pH 7.0. Before inoculating the samples, the serum bottles were deaerated with inert gas. Before autoclaving, the bottles were sealed with butyl rubber septa and aluminum caps. Following enrichment by employing selective enrichment techniques with glucose as the carbon source, the bacterial samples were subjected to isolation.

Example 2

This example illustrates the isolation and identification of lactic acid producing bacterium E. faecalis CBRD01. Enrichment cultures displaying positive growth with high lactic acid after 2 to 3 consecutive transfers in selective media were chosen for isolation. To isolate lactate producing microorganisms, the selective media was supplemented with 50 mM glucose. The lactate producing microbial culture was streaked on to an agar plate containing selective media and denied oxygen. About 55 different microbial strains were isolated from the samples. Cultures that displayed rapid growth on glucose with lactic acid as the primary metabolite were resorted for further isolation and their purity was verified by streaking on medium solidified with agar. The purified isolate with lactate producing capability on glucose and minimal nutrients is referred to as CBRD01. According to the cell morphology, cellular fatty acid composition and biochemical reactions (shown below in Table 1), the isolate CBRD01 was identified by DSMZ (Braunschweig, Germany) as *Enterococcus faecalis* and named *Enterococcus faecalis* CBRD01.

TABLE 1

Biochemical characterization of E. faecalis CBRD01

| Characteristics | Reaction |
| --- | --- |
| Shape | Cocci (elongated) |
| Size (in diameter) | 1.2–1.5 |
| Gram-reaction | + |
| Aminopeptidase | − |
| KOH | − |
| Oxidase | − |
| Catalase | − |
| Acid from | |
| Trehalose | + |
| Mannitol | + |
| Raffinose | − |
| Lactose | + |
| Ribose | + |
| Saccharose | + |
| Arabinose | − |
| Melibiose | − |
| Sorbitol | + |
| Melezitose | + |
| L-Rhamnose | − |
| Cellobiose | + |
| Mannose | + |
| Inositol | + |
| ADH | + |
| Urease | − |
| Voges Proskauer | + |
| β-Galactosidase | − |
| Alkaline Phosphatase | − |

TABLE 1-continued

Biochemical characterization of E. faecalis CBRD01

| Characteristics | Reaction |
| --- | --- |
| Growth at 45° C. | + |
| Growth at 50° C. | − |

Example 3

This example illustrates the lactic acid production characteristics in *E. faecalis* CBRD01 at shake flask scale. To demonstrate the production of lactic acid in *E. faecalis* CBRD01, the strain was cultured in serum bottles as described in Example 1. Before inoculation, the serum bottles were deaerated, sealed with butyl rubber septa, closed with aluminum caps and autoclaved. The flasks were inoculated with cells of *E. faecalis* CBRD01 (initial $OD_{600}$ of 0.2±0.01). Fermentation was carried out under anaerobic conditions at 37° C. while agitated. Samples were withdrawn periodically to determine cell mass, residual glucose and metabolites.

Table 2 shows the effect of glucose concentration on lactate production in *E. faecalis* CBRD01. A maximum yield was obtained when the cells were grown in 100 mM glucose, while the yield was slightly decreased at 50 mM and 25 mM glucose. On average, 27 to 31 mM of glucose was consumed regardless of the initial glucose concentration, whereas the lactate production was between 49 to 61 mmol per liter.

TABLE 2

Batch production of lactate by E. faecalis CBRD01 in shake flasks

| Initial glucose concentration (mM) | Glucose consumed (mM) | Lactate titer (mmol/L) | Lactate yield (mol/mol glucose) | Lactate yield (%) |
| --- | --- | --- | --- | --- |
| 28.79 | 26.87 | 49.12 | 1.83 | 91.40 |
| 56.13 | 33.91 | 60.84 | 1.79 | 89.71 |
| 110.22 | 30.55 | 60.21 | 1.97 | 98.54 |

Example 4

This example illustrates the lactic acid production characteristics of *E. faecalis* CBRD01 at bioreactor scale. In the shake flask experiments, illustrated in Example 3, *E. faecalis* CBRD01 exhibited the highest lactate yield of 98.54% on 100 mM glucose after 12 h of fermentation, beyond which point the lactate production ceased due to a drop in pH below 5.0. In order to further investigate the lactate producing potential of *E. faecalis* CBRD01 under controlled pH conditions, the strain was cultured at neutral pH.

TABLE 3

Batch production of lactate by E. faecalis CBRD01 in a fermentor

| Fermentation parameters | Cultivation time | |
| --- | --- | --- |
| | 0–12 h | 12–24 h |
| Glucose utilized (mmol $l^{-1}$) | 57.04 | 37.02 |
| Glucose specific uptake rate, $v_{max}$ (mmol $l^{-1}$) | 37.96 | 7.75 |
| Maximum specific growth rate, $\mu_{max}$ ($h^{-1}$) | 0.59 (0-3 h) | — |
| Lactate produced (mmol $l^{-1}$) | 100.25 | 72.55 |
| Lactate specific production rate, $q_{max}$ (mmol $g^{-1}$ cdw $h^{-1}$) | 66.72 | 15.20 |

TABLE 3-continued

Batch production of lactate by *E. faecalis* CBRD01 in a fermentor

| Fermentation parameters | Cultivation time | |
|---|---|---|
| | 0–12 h | 12-24 h |
| Lactate yield (mol mol$^{-1}$ glucose) | 1.75 | 1.96 |
| Lactate yield (g g$^{-1}$ glucose) | 0.88 | 0.98 |

Lactate was the major fermentation product with other metabolites, such as acetate and formate, produced at low quantities (less than 1 g/l in the 1$^{st}$ phase, and less than 0.1 g/l) in the 2$^{nd}$ phase (Table 4). No $CO_2$, ethanol or other metabolites were produced. Overall, the acetate and formate represented less than 6% of the total amount of metabolites produced by *E. faecalis* CBRD01.

TABLE 4

Batch production of metabolites by *E. faecalis* CBRD01 in a fermentor

| Metabolite | Phase 1 (0-12 h) | | Phase 2 (12-24 h) | | Combined (0-24 h) | |
|---|---|---|---|---|---|---|
| Lactate | 9.03 g l$^{-1}$ | 90.85% | 6.59 g l$^{-1}$ | 98.95% | 15.62 g l$^{-1}$ | 94.10% |
| Acetate | 0.39 g l$^{-1}$ | 3.92% | 0.04 g l$^{-1}$ | 0.60% | 0.43 g l$^{-1}$ | 2.59% |
| Formate | 0.52 g l$^{-1}$ | 5.23% | 0.03 g l$^{-1}$ | 0.45% | 0.55 g l$^{-1}$ | 3.31% |

The carbon material balance and distribution analysis revealed that 87.88% of the glucose carbon was directed to lactate at the phase 1, while 6.2% of carbon was directed to biomass formation. However, no carbon was directed to biomass and other metabolites such as acetate and formate in the second phase, thus yielding 98% of lactate. The electron balance analysis indicates that the electrons released during glucose oxidation have been completely recovered in the form of products. Based on the carbon and electron distribution balances, a homolactic fermentative pathway for lactic acid production in *E. faecalis* CBRD01 has been proposed.

Example 5

This example illustrates the lactic acid production by *E. faecalis* CBRD01 in a fed-batch mode at bioreactor scale. The fed-batch process was carried out under anaerobic conditions in a glass jar reactor (DASGIP) at pH 7.0 and 37° C. using the salt mineral medium described in Example 1. Prior to inoculation, the fermentor was deaerated to ensure that it was free of $O_2$. The bioreactor was inoculated with *E. faecalis* CBRD01 cells, grown under anaerobic conditions prior to fermentation. This experiment produced the highest lactate yield (91 to 97%) in the initial phase of incubation.

Example 6

This example illustrates the lactic acid production by *E. faecalis* CBRD01 in a fed-batch mode at bioreactor scale using a higher density cell culture. In order to increase the lactate yield and productivity and meet the industrial requirements for lactic acid production of at least 100 g/L as the titer, with 80% yield and 2.5 g/L/h as the volumetric productivity, an improved fed-batch process was conducted in glass jars in parallel bioreactors (DASGIP) Two different media were utilized:
1. A complex medium containing (per liter of deionized water): yeast extract, tryptone, dipotassium phosphate, monopotassium phosphate buffer, and glycerol.
2. A mineral salt medium according to Example 1.

The pH of both culture media was maintained at neutral pH 7.0. The fermentors were deaerated as described in Example 5. The initial glucose concentration was the same in both fermentors. Fermentation was initiated by adding *E. faecalis* CBRD01 cells, grown under anaerobic conditions. The fermentation process was carried out at 37° C.

After fermentation in the complex medium, *E. faecalis* CBRD01 was able to produce 2,021.65 mmol lactate/L, with an average volumetric productivity of 4.79 g/L/h. The total glucose consumption accounted for at the end of fermentation was 210.01 g, therefore, the overall lactate yield in the complex medium was 86.7% of the theoretical maximum of glucose, or 1.73 mol/mol glucose. The microbial biomass production was 16.86 g cdw/L at the end of fermentation.

After 38 h of fermentation in the mineral salt medium, *E. faecalis* CBRD01 was able to produce 1,283.55 mmol lactate/L, with an average volumetric productivity of 3.04 g/L/h. The microbial biomass production was 9.93 g cdw/L at the end of fermentation.

Overall, the fed-batch production of lactate by *E. faecalis* CBRD01 in both media resulted in higher lactate titer, productivity and yield compared to batch production of lactate that meets or exceeds the industrial requirements for commercial production of lactic acid.

TABLE 5

Fed-batch production of lactate using high density culture of *E. faecalis* CBRD01

| Fermentation medium | Cell density (g l$^{-1}$) | Fermentation time (h) | Glucose consumed (g l$^{-1}$) | Lactate titer (g l$^{-1}$) | Lactate yield (%) | Lactate productivity (g l$^{-1}$ h$^{-1}$) |
|---|---|---|---|---|---|---|
| Complex | 22.0 | 13 | 146.11 | 133.71 | 91.5 | 10.29 |
| Mineral salt | 9.8 | 15 | 115.98 | 113.43 | 97.8 | 7.56 |

Example 7

In order to increase the commercial applications of the isolated organism *Enterococcus faecalis* CBRD01, it is desirable for the organism to be resistant to the lowered pH of the desired product, lactic acid. It is also desirable from a commercial standpoint to be able to isolate lactic acid directly from the medium without acidification. Thus, the inventors sought to produce a derivative that grows well and produces high level of lactic acid at lower pH. A "genome shuffling" procedure was used to direct the evolution toward productivity at low pH, wherein cells are fused as protoplasts, allowing mixing of genetic material. Deleterious mutations are selected against, and the desired phenotype can be obtained.

For directed evolution of *E. faecalis* CBRD01 using genome shuffling, *E. faecalis* CBRD01 was treated in two ways. One culture was mutagenized with nitrosoguanidine, and subsequently spread on medium plates with pH ranging from 6.0 to 3.0 in half pH unit increments. Two separate libraries were made by pooling the survivors from the pH 3.0, 3.5 and 4.0 plates (Pop1) and the pH 4.5 and 5.0 plates (Pop2).

A separate culture of unmutagenized *E. faecalis* CBRD01 was grown repeatedly in liquid culture with decreasing pH, a process that spanned several weeks. The outcome was an evolved strain, *E. facaelis* CBRD0153, which appeared to grow as well at pH 5.3 as the original parent strain did at pH 6.0. At the same time, the lactic acid concentration was 21% higher at pH 5.3 than 6.5 after 24 h of incubation in the same fermentation medium. This strain was then spread on medium plates with pH ranging from 6.0 to 3.0. Two separate libraries were also made by pooling survivors of the pH 3.0 and 3.5 plates (Pop3) and pH 4.0 and 4.5 (Pop4).

Cultures of all 4 populations were treated to form protoplasts, and then fused in polyethylene glycol in pairwise combinations: Populations 1 and 2 were each fused with Populations 3 and 4. In addition, a fusion of all four populations was made. The resulting five fusions (Pop1+Pop3; Pop1+Pop4; Pop2+Pop3; Pop2+Pop4; Pop1+Pop2+Pop3+Pop4) were regenerated on plates, and the survivors used to inoculate fresh medium to be used in subsequent recursive protoplast fusions. Following each round of fusion and regeneration, cells were tested on pH plates from 6.0 to 3.0. With each round, more vigorous growth was seen at decreasing pH. These resulting isolates are previously un-described, acid-tolerant, lactic-acid producing *E. faecalis* CBRD01.

Individual acid-tolerant isolates purified from the last regenerated fusion, and tested for growth at low pH, as well as lactic acid production, are predicted to show resistance to the lowered pH of the desired product, lactic acid. Further, individual isolates purified from the last regenerated fusion are predicted to permit isolation of lactic acid directly from the medium without acidification.

Example 8

Cloning and Expression of LDH Genes from *E. faecalis* CBRD01

This example illustrates procedures for analyzing the expression and cloning of LDH1 and LDH2 genes from *E. faecalis* CBRD01. DNA and RNA were purified from of *E. faecalis* CBRD01 grown under anaerobic and aerobic conditions in MRS Broth (DIFCO). DNA was purified using standard procedures involving lysis, phenol and chloroform extractions, and ethanol precipitation. RNA was purified using Thermo Scientific GeneJET RNA Purificaiton Kit (#K0731).

First Strand cDNA synthesis was performed using primers specific for both LDH genes using Thermo Scientific Maxima Reverse Transcriptase. Primers for qPCR comprised the following sequences: LDH1-5' CGGAGATACAGAATTC-CCAGTTT 3' (Sense; SEQ ID NO:5); 5' CTTTAGT-GATACGCGCTAGT 3' (AntiSense; SEQ ID NO:6); LDH2-5' AGTGGCTGTCTGGTCTCATA 3' (Sense; SEQ ID NO:7); 5' GCCCATATTGCCCATCTAAGT 3' (AntiSense; SEQ ID NO:8). Primers for 5S RNA, used as an internal control, were 5S Forward 5' TGGCGATAGCGAGAAG-GATA 3' (SEQ ID NO:9) and 5S Reverse 5' GTCCTACTCT-CACAAAGGGAAAC 3' (SEQ ID NO:10). Gene expression was quantitated using qPCR under anaerobic and aerobic growth, with a particularly good expression of the LDH1 gene occurring in *E. faecalis* CBRD01.

Cloning the LDH1 and LDH2 genes required amplification of genes with added restriction adaptors for cloning. The following primers provided robust amplification of these genes: 1) LDH1 primers with restriction sites for cloning: 'GCCAAGCTTTTGAAGATTAAGAAAGATGTA 3' (SEQ ID NO:11) and 5'GGAATTCTTATTTTGCTTCTTCT-GCTTC 3' (SEQ ID NO:12); 2) LDH2 primers with restriction sites for cloning: 5'GCCAAGCTTATGAAAGTATT-TAACAAAAAAGTC 3' (SEQ ID NO:13); and 5'GGAATTCCTAAGCGTTCGGTTGTAACGA 3' (SEQ ID NO:14). The above PCR products can be directionally cloned in-frame into expression vectors for expression and over expression. This description provides a representative example of expression analyses and cloning capabilities with the LDH genes from *E. faecalis* CBRD01 and is not meant to limit or exclude other embodiments of the extant invention.

Example 8

Sequences used in exemplary embodiments of the invention. The coding sequences in the DNA sequences are underlines, and start codons are in bold. Note the LDH 2 (RNHR01261) has a TTG as start codon instead of ATG and therefore the corresponding first amino acid in RNHR01261 is "L"

SEQ ID NO: 1
Lactate Dehydrogenase Gene 1 (RNHR02052)
ATAACAAAAAAAGCACGCTTCCCTTATTTAAATTGTTAATAAAGACTATT

ACAGATTGGTATAACCACACCTAAAAAGTTCGTGATATAATTCACTAAGA

AAGAAATATTACAGAAAGAAGAGATGAACGATGAAAGTATTTAACAAAAA

AAGTCGCAATTATTGGTACTGGTTTTGTTGGCACAAGTATTGCCTATTCC

ATGATCAACCAAGGGATTGCGAATGAATTAATCTTAGTTGATATTGACAA

AGCCAAATCTGAAGGCGAAGCAATTGACTTATTAGATGGTGTGTCTTGGG

GTCAAGAAAATGTAAACGTCTGGGCTGGCGACTATCAAGACTGCCAAGAT

GCCGATATCGTCGTGATTACAGCTGGCGCTAATCAAAAACCTGGGCAAAG

TCGTCTAGATTTGGTTTCAATCAATGCAGAAATTATGAAAACAATTGTTA

ACAATATCATGAAATCTGGTTTTGATGGAATTTTAGTGATTGCCTCAAAT

CCTGTCGATGTACTGACTTATGTGGCTTGGCAAGCTTCTGGTTTACCTGT

TTCAAGAGTAATTGGAACTGGTACAACTTTGGACACAACTCGTTTCCGCA

AAGAACTGTCTCAACGTTTAGCGATTGATCCACGCAATGTTCACGGCTAT

ATTATTGGCGAACACGGGGATTCTGAAGTGGCTGTCTGGTCTCATACCAT

GATTGGTACCAAACCTATTTTAGAAATTGTGGATACGACAGAGCGCTTAA

CTAGTGACGATTTACCAATCATTTCTGATAAAGTGAAAAATACAGCTTAT

GAAATTATCGATCGCAAACAAGCGACCTATTATGGGATTGGTATGAGTAC

TGCACGCATTGTTAAAGCCATTTTAAATAATGAACAAGCTATTTTACCTG

TCTCAGCTTACTTAGATGGGCAATATGGGCAACAAGATGTATTTACAGGG

ATTCCTGCAGTCGTTGGCAATCAAGGTGTGACTGACATTATTGAATTGAA

TCTGAATGCCGCTGAAAAAGAACTCTTCCAAAAATCAGTGACACAATTAA

AACAAGTGATGGCATCGTTACAACCGAACGCTTAGTAATTTTTAACTAAA

AATAACACTTCAACTAAATTATTCTCTACCAAAATAGATTCTAATTCCCC

TTTATCGTTCTTTTTGGTACCATGAAAGAAGAACTTCAACTAAAGCAGAA

ATTAGGAGGACAAAAAATGGTAATCCAAGGAGATACGTTAGAAAATAGCG

CACGTCGTTTATTGCAAGAACGTGGCGTAACA

SEQ ID NO: 2
Lactate Dehydrogenase Gene 2 (RNHR01261)
TTGAAGATTAAGAAAGATGTAAAAAAATTTTTTAGAAATTTAAATATGCG

CAAGATAGTGAAATTACGCACATGTAAGAGCTACCATTTTGAAACAGGTC

TGAAAACTGTATCATTTTTACAATCAAAGTTCGTGACATTTTTTACAAAC

CATGTTACTATCACTTTAGCAACAGGAAATAAAAACTCGTTGCTCACGAA

AAAGAATGTAGAGGAAGGAATGGTACACATGACTGCAGCCGCAGGGAATA

AAGATCACCAAAAAGTAATTTTAGTCGGGGACGGTGCCGTAGGTTCTAGC

TATGCCTTTGCTTTAGTAACTCAGAATATTGCTCAAGAAGTTGGGATTAT

TGATATTAATGTACCAAAAACTGAAGGAGACGCGTTGGACTTATCTCACG

CATTAGCATTTACTTCTCCTAAAAAAATCTATGCTGCTACTTATGACGAT

TGCCATGATGCAGACTTAGTTGTCTTAACAGCTGGTGCGCCTCAAAAACC

AGGCGAAACTCGTTTAGACTTAGTTCATAAAAACTTGAAAATTAATAAAG

AAATCGTTACAACAATTGTTGATTCTGGTTTCAACGGTATCTTCTTAGTT

GCCGCAAACCCAGTTGATATTTTGACTTATTCAACTTGGAAATTCTCTGG

CTTCCCGAAAGAACGAGTAATCGGTTCAGGAACTTCACTAGATTCTGCTC

GTTTCCGTCAAGCAATTGCCGAATTAGTTGATGTTGATGCACGAAATGTC

CATGCCTACATCTTAGGGGAACACGGAGATACAGAATTCCCAGTTTGGTC

ACATGCGAATGTCGCTGGCTTACAAATTTACGAATGGGTGAAAAATAATC

CTGACGTCGATGAAGAAGCAATGGTTAATTTATTCTTCAACGTACGCGAC

GCTGCTTACACAATCATCGAGAAAAAAGGAGCTACTTTCTATGGAATCGC

GGTTGCACTAGCGCGTATCACTAAAGCTATCCTAAACGATGAAAACTCTG

TGTTACCATTATCTGTTTATTTAGAAGGTGAATATGGTCAAAACGATATT

TATATCGGTGCACCAGCGATCATCAACCGCCAAGGAGTTAAACAAGTCAT

TGAAATTCCATTAACAGATGCTGAACAAGAAAAAATGGAAGCTTCTGCTT

CTGCATTAAAAGAAGTTATTGAAACAGCTTTTGCTAAATTTGAAGCAGAA

GAAGCAAAATAA

SEQ ID NO: 3
The corresponding amino acid sequence
of RNHR02052
MKVFNKKVAIIGTGFVGTSIAYSMINQGIANELILVDIDKAKSEGEAIDL

LDGVSWGQENVNVWAGDYQDCQDADIVVITAGANQKPGQSRLDLVSINAE

IMKTIVNNIMKSGFDGILVIASNPVDVLTYVAWQASGLPVSRVIGTGTTL

DTTRFRKELSQRLAIDPRNVHGYIIGEHGDSEVAVWSHTMIGTKPILEIV

DTTERLTSDDLPIISDKVKNTAYEIIDRKQATYYGIGMSTARIVKAILNN

EQAILPVSAYLDGQYGQQDVFTGIPAVVGNQGVTDIIELNLNAAEKELFQ

KSVTQLKQVMASLQPNA

SEQ ID NO: 4
The corresponding amino acid sequence
of RNHR01261
LKIKKDVKKFFRNLNMRKIVKLRTCKSYHFETGLKTVSFLQSKFVTFFTN

HVTITLATGNKNSLLTKKNVEEGMVHMTAAAGNKDHQKVILVGDGAVGSS

YAFALVTQNIAQEVGIIDINVPKTEGDALDLSHALAFTSPKKIYAATYDD

CHDADLVVLTAGAPQKPGETRLDLVHKNLKINKEIVTTIVDSGFNGIFLV

AANPVDILTYSTWKFSGFPKERVIGSGTSLDSARFRQAIAELVDVDARNV

HAYILGEHGDTEFPVWSHANVAGLQIYEWVKNNPDVDEEAMVNLFFNVRD

AAYTIIEKKGATFYGIAVALARITKAILNDENSVLPLSVYLEGEYGQNDI

YIGAPAIINRQGVKQVIEIPLTDAEQEKMEASASALKEVIETAFAKFEAE

EAK

The examples set forth above are provided to give those of ordinary skill in the art a complete disclosure and description of how to make and use embodiments of the compositions, and are not intended to limit the scope of what the inventors regard as their invention. Modifications of the above-described modes (for carrying out the invention that are obvious to persons of skill in the art) are intended to be within the scope of the following claims. All publications, patents and patent applications cited in this specification are incorporated herein by reference as if each such publication, patent or patent application were specifically and individually indicated to be incorporated herein by reference.

What is claimed is:

1. A genetically modified lactic acid producing *Enterococcus faecalis* bacterium, comprising a polynucleotide encoding a lactate dehydrogenase, wherein said polynucleotide comprises a nucleotide sequence selected from the group consisting of:
   (a) a nucleotide sequence having at least 95% sequence identity across the entire polynucleotide to the sequence of SEQ ID NO: 1 or 2 wherein said nucleotide sequence encodes a lactate dehydrogenase; or
   (b) a nucleotide encoding a protein having at least 95% sequence identity to SEQ ID NO: 3 or 4 and having lactate dehydrogenase activity; and
wherein lactic acid production is conducted at a pH between 5.0 and 3.0.

2. The lactate dehydrogenase producing *E. faecalis* of claim 1 wherein said microorganism is derived from *E. faecalis* CBRD01 (ATCC Accession Number TA-12846).

3. The lactic acid producing *E. faecalis* of claim 1, wherein said lactate dehydrogenase converts pyruvate and reduced nicotinamide adenine dinucleotide (NADH) into lactic acid and oxidized nicotinamide adenine dinucleotide (NAD+).

4. The lactic acid producing *E. faecalis* of claim 1 wherein said microorganism is capable of producing lactic acid at a pH less than 6.

5. The lactic acid producing *E. faecalis* of claim 1, wherein said *E. faecalis* converts at least 80% of an available carbon source into lactic acid.

* * * * *